United States Patent [19]
Pai et al.

[11] Patent Number: 5,788,925
[45] Date of Patent: Aug. 4, 1998

[54] METHOD FOR REAL TIME MONITORING AND CONTROL OF LOAD STERILIZATION AND PARAMETRIC RELEASE

[75] Inventors: Sanjeeth M. Pai, Cary; Peter E. Zell, Raleigh, both of N.C.

[73] Assignee: Steris Corporation, Mentor, Ohio

[21] Appl. No.: 602,515

[22] Filed: Feb. 16, 1996

[51] Int. Cl.[6] .................................................. A61L 2/24
[52] U.S. Cl. ........................ 422/3; 73/865.9; 374/142; 374/143; 364/500; 422/26; 422/28; 422/34; 422/36
[58] Field of Search ..................... 73/865.9; 374/142, 374/143; 364/500; 422/3, 26, 28, 34, 36, 108–110, 119, 292

[56] References Cited

U.S. PATENT DOCUMENTS

| | | |
|---|---|---|
| 3,861,875 | 1/1975 | Joslyn ........................... 21/103 |
| 3,982,893 | 9/1976 | Joslyn . |
| 4,067,691 | 1/1978 | McGady . |
| 4,164,538 | 8/1979 | Young . |
| 4,203,947 | 5/1980 | Young . |
| 4,261,950 | 4/1981 | Bainbridge . |
| 4,309,381 | 1/1982 | Chamberlain . |
| 4,594,223 | 6/1986 | Dyke . |
| 4,687,635 | 8/1987 | Kaehler . |
| 4,839,291 | 6/1989 | Welsh . |
| 4,914,034 | 4/1990 | Welsh . |
| 5,164,161 | 11/1992 | Feathers . |
| 5,258,921 | 11/1993 | Ellis . |
| 5,270,948 | 12/1993 | O'Brien . |
| 5,290,511 | 3/1994 | Newman . |
| 5,340,537 | 8/1994 | Barrett . |
| 5,368,821 | 11/1994 | Schmoegner . |
| 5,380,485 | 1/1995 | Takahashi . |
| 5,390,322 | 2/1995 | O'Brien . |
| 5,413,757 | 5/1995 | Kutner . |
| 5,422,276 | 6/1995 | Colvin . |
| 5,426,428 | 6/1995 | Binder et al. ................... 340/870.17 |
| 5,478,749 | 12/1995 | Dyke . |
| 5,491,092 | 2/1996 | Colvin . |
| 5,565,634 | 10/1996 | Graessle et al. ................ 422/119 |

FOREIGN PATENT DOCUMENTS

| | | |
|---|---|---|
| 9319369 U | 4/1995 | Germany . |
| WO 93/21964 | 11/1993 | WIPO . |
| WO 95/32742 | 12/1995 | WIPO . |

OTHER PUBLICATIONS

International Organization for Standardization, ISO/TC 198/WG 3, Feb. 1995, 5.2.5.

Hücker, G., 1995, The Steriguard System: A New Measuring System for Batch Control in Steam Sterilisation. Zentr. Steril. 3: 131–135.

Primary Examiner—Peter A. Kruskoci
Attorney, Agent, or Firm—Fay, Sharpe, Beall, Fagan, Minnich & McKee

[57] ABSTRACT

The invention is a system and method for real-time monitoring and control of sterilization cycle parameters within a load-simulation device that simulates the same conditions as those within an acceptable standard challenge load to be sterilized. Integration of the device into the sterilizer control system allows critical sterilization parameter levels to be achieved and maintained within the simulated load throughout a sterilization cycle, thus resulting in a significant reduction in the number of unsuccessful cycles. A redundant parameter-monitoring system within the device is included. When acceptable sterilization parameter levels are shown to have been met, the sterile load is automatically released for use immediately upon completion of the cycle, thus eliminating the need for biological indicators and chemical integrators.

14 Claims, 7 Drawing Sheets

METHOD FOR REAL TIME MONITORING AND CONTROL OF LOAD STERILIZATION AND PARAMETRIC RELEASE

BACKGROUND

Monitoring of sterilization parameters is essential to ensure that optimum sterilizing conditions during a steam or chemical sterilization cycle are met. Environmental conditions in the chamber are frequently measured by various sensors, such as temperature, pressure, or sterilant concentration sensors, positioned in strategic places, such as a chamber wall or a drain line. The sensors, in turn, may be connected by various methods (e.g. electrical, radio transmitter, etc.) to an integral or remote microprocessor controller programmed to monitor and respond to the sensor readings and provide control of critical cycle parameters in the chamber, such as temperature, pressure, relative humidity, sterilant concentration and time during the cycle.

Control of cycle parameters in the chamber, however, does not guarantee that sterilization conditions have been met within the load to be sterilized. Systems have been developed employing temperature and pressure sensors placed within an actual load or in standardized devices simulating a load. Each of these prior systems has disadvantages. For example, a sensor placed in an actual load monitors a condition only at the sensor location and does not necessarily reflect the condition elsewhere in the load. Load simulation devices, such as those containing a heat sink to detect the presence of air or superheated steam or those containing sensors to monitor and record time, temperature, pressure and/or moisture, have the disadvantage that the load-simulation devices are not integrated with the sterilizer control system and are monitors only. In some, information is available only after the sterilization cycle, when the device is removed from the chamber and the record of a parameter is interpreted visually (e.g. a color change) by the operator. In others, the monitored information is transmitted to an external stand-alone control and display unit, adding to the expense of a sterilization system. Neither approach provides the capability of real-time monitoring of critical load parameters with direct and simultaneous conveyance of the information to the sterilizer control system allowing real-time control of critical sterilization parameter levels within the load. Further, prior load-simulation devices monitor only such parameters as temperature, pressure, time, moisture or the presence of a sterilant. They do not provide the capability of also directly monitoring the concentration of a chemical sterilant, such as ethylene oxide gas or hydrogen peroxide liquid or vapor, in a load, or of directly conveying the results to the sterilization control for real-time control of the sterilant concentration in the load.

Currently, the Association for Advancement of Medical Instrumentation (AAMI) guidelines recommend that chemical integrators and biological indicators be used to verify that process parameters critical for sterilization have been achieved. Chemical integrators provide a visual indication (e.g. a color change) that predetermined sterilization parameters were presumably achieved; for example, in the case of steam or ethylene oxide sterilization, a chemical integrator might indicate that a given temperature with the presence of moisture was achieved for a given time. Chemical integrators, however, are not sophisticated enough to monitor critical cycle parameters (e.g. temperature, pressure, sterilant concentration) to a confidence level that would assure that sterilization has occurred and to allow release of the load for use based on the indicator results alone.

Therefore, biological indicators are additionally employed. Presumably, if proper conditions in the chamber with respect to time, temperature, pressure and/or sterilant concentration are achieved and maintained for the required exposure period, the biological agent in the indicator will be killed, and thereby indicate cycle efficacy. However, the requirement for a sometimes lengthy incubation of the biological indicator to assure confirmation of sterility can result in an undesirable time delay after cycle completion before the sterilization efficacy is known. This delay can significantly affect productivity and, therefore, the cost of processing goods through the sterilization system, in addition to the inconvenience of delayed turnaround of critical medical or dental instruments.

Recently, the concept of parametric release has been described for moist heat sterilization, and seeks to provide a more efficient means for monitoring a steam sterilization process. Parametric release is based on the physical monitoring in the chamber of the parameters of pressure, temperature and rate of change of temperature and pressure during the moist heat sterilization cycle. The chamber control is set for a predetermined cycle, to achieve and maintain predetermined critical parameter levels for a given period of time. The chamber parameters are monitored throughout the cycle. If the monitoring indicates a difference between a set and measured parameter value that exceeds specified limits, a warning is given to the cycle operator. If the monitoring indicates that the critical levels in the chamber are achieved and maintained for the time required to achieve a given sterility assurance level, the cycle is considered efficacious and the load is released for use. Therefore, parametric release systems are designed to provide monitoring and notification only of achieved parameters in the chamber. They do not suggest providing real-time sensing data to the sterilizer control system to enable the sterilizer control to react to changes in the critical parameters and adjust them in order to avoid unsuccessful cycles. Rather, current International Organization For Standardization (ISO) and European Committee for Standardization (CEN) standards require that the monitoring system for parametric release be separate from the sterilizer control system. Further, the process is described only for control of parameters in the chamber and does not address the monitoring and control of the critical parameter levels in the load itself.

A need exists, therefore, for a sterilization system that provides both real-time monitoring and real-time control of critical sterilization parameters in the load, to a sterility assurance level that eliminates the need for chemical and biological indicators. There is a further need for a device that provides real-time monitoring of critical sterilization parameters in the load, and is also integrated with the sterilizer control system to enable the control to react to monitored changes in the critical parameter levels and adjust them in real-time in order to avoid unsuccessful cycles. There is a further need for a device that reproducibly simulates a standard challenge load undergoing sterilization and that contains critical parameter sensors that are directly integrated into the sterilizer control system. There is further a need for a sterilization system that provides for the release of a load when the critical values of sterilization parameters in the load are shown to have been met.

SUMMARY OF THE INVENTION

The present invention provides real-time monitoring and control of sterilization cycle parameters, during a sterilization cycle, within a load-simulating device that simulates the same conditions as those which would be found in an acceptable standard challenge load to be sterilized. The levels of critical load sterilization parameters, such as temperature, pressure, relative humidity, and sterilant concentration are sensed by sensor probes positioned within the load-simulating device and the data transmitted directly, in real-time, to the sterilizer control system. The control system then provides real-time control of critical parameter levels within the simulated load device.

A redundant set of sensor probes within the device also monitors the sterilization parameters in real-time and transmits the sensed data to a parametric release monitoring system. If the monitored sterilization parameter levels indicate sterilization cycle efficacy (as measured by the conditions sensed within the load-simulating device), the load is released for use immediately upon completion of the sterilization cycle. Thus, the present invention eliminates the need for chemical integrators and biological indicators and increases the efficiency of sterilization.

The load-simulation device of the invention comprises a resistance barrier to penetration of a sterilant and a receiving area for the sterilant that penetrates the resistance barrier. Sensor probes are positioned in the receiving area for sensing and transmitting data to the sterilizer control system. A parametric control means controls the value of a sterilization parameter in real time during the sterilization cycle, in response to a signal from the sterilizer control system. The sterilizer control system is programmed to store a predetermined reference sterilization parameter range, to receive the sensed parameter value and compare the sensed value to the reference range, to indicate acceptable sterilization conditions when the sensed parameter value falls within the reference parameter range, and to signal the parameter control means to change the value of the sterilization parameter when the sensed value falls outside the reference range. A redundant set of sensor probes senses and transmits data to a parametric release system.

The present invention may be used with sterilization systems including, but not limited to, steam, ethylene oxide gas, liquid and vaporized hydrogen peroxide, liquid and vaporized formaldehyde, liquid and vaporized peroxy compounds, ozone, ionized gases, plasmas, and combinations thereof.

The invention also includes a sensor fitting for connecting the load-simulating device to a sterilization chamber and a sensor probe. A method for monitoring and controlling a sterilization parameter value in a simulated load during a sterilization cycle is also provided.

DETAILED DESCRIPTION

The present invention is concerned with the real-time control of sterilization cycle parameters within a load-simulation device that simulates the same conditions as those within an acceptable standard challenge load to be sterilized. Integration of such a load-simulating device into a sterilization chamber parameter sensing system allows real-time monitoring and transmission of cycle parameter values from the load-simulating device to the sterilizer control system. If the parameter values fall outside the range of acceptable values, the sterilizer control system directs the operation of control means, such as heaters, valves, pumps, timers, etc. in real time to bring the parameter values into an acceptable range within the load-simulating device. Thus, optimum and efficacious sterilization conditions can be achieved and maintained within the load (as measured by the conditions sensed within the load-simulating device) resulting in a significant reduction in the number of unsuccessful cycles. Moreover, when acceptable sterilization parameters are shown to have been met, the sterile load is automatically released for use immediately upon completion of the cycle. Thus, the need for biological indicators and chemical integrators is eliminated.

The invention may be used with any sterilization process in which a successful outcome depends on achieving and maintaining controllable sterilization parameters for a given time. Such sterilization processes include, but are not limited to, sterilization with steam, ethylene oxide gas, liquid and vaporized hydrogen peroxide, liquid and vaporized formaldehyde, liquid and vaporized peroxy compounds, ozone, ionized gases, plasmas, and combinations thereof.

The load-simulating device of the invention is integrated into the sterilizer parameter sensing and control system and employs one or more resistance barriers to penetration of the sterilant, in the form of a tortuous path, similar to the barrier encountered by a sterilant penetrating a load of wrapped goods or goods in a sealed pouch. The acceptable standard challenge load simulated by the load-simulating device reflects a "worst-case" load to be sterilized. Therefore, each type of resistance barrier in the load-simulating device is specifically designed for the particular sterilant to be employed in order to accurately simulate load conditions, or worst-case conditions, using the specified sterilant. For example, for sterilants such as hydrogen peroxide vapor, a sufficient resistance barrier may comprise a tortuous path for entrance of the sterilant into the device. For other sterilants, such as ethylene oxide gas, the resistance barrier may additionally or alternatively comprise another tortuous path within the interior of the device, such as a packed material or a baffle or series of baffles. The resistance barrier may be purely a physical barrier and/or may also comprise a physical or chemical material which is slightly absorptive of the sterilant. Suitable resistance barrier materials may include, but are not limited to, cellulosic materials for steam and/or ethylene oxide sterilants, teflon, silicon, polypropylene and polycarbonate materials for ethylene oxide and/or hydrogen peroxide sterilants, and combinations thereof. Effective resistance barrier materials for other sterilants, such as formaldehyde, ozone, or ionized gases and plasmas, are known to persons skilled in the art of sterilization.

Figures 1A, 1B:
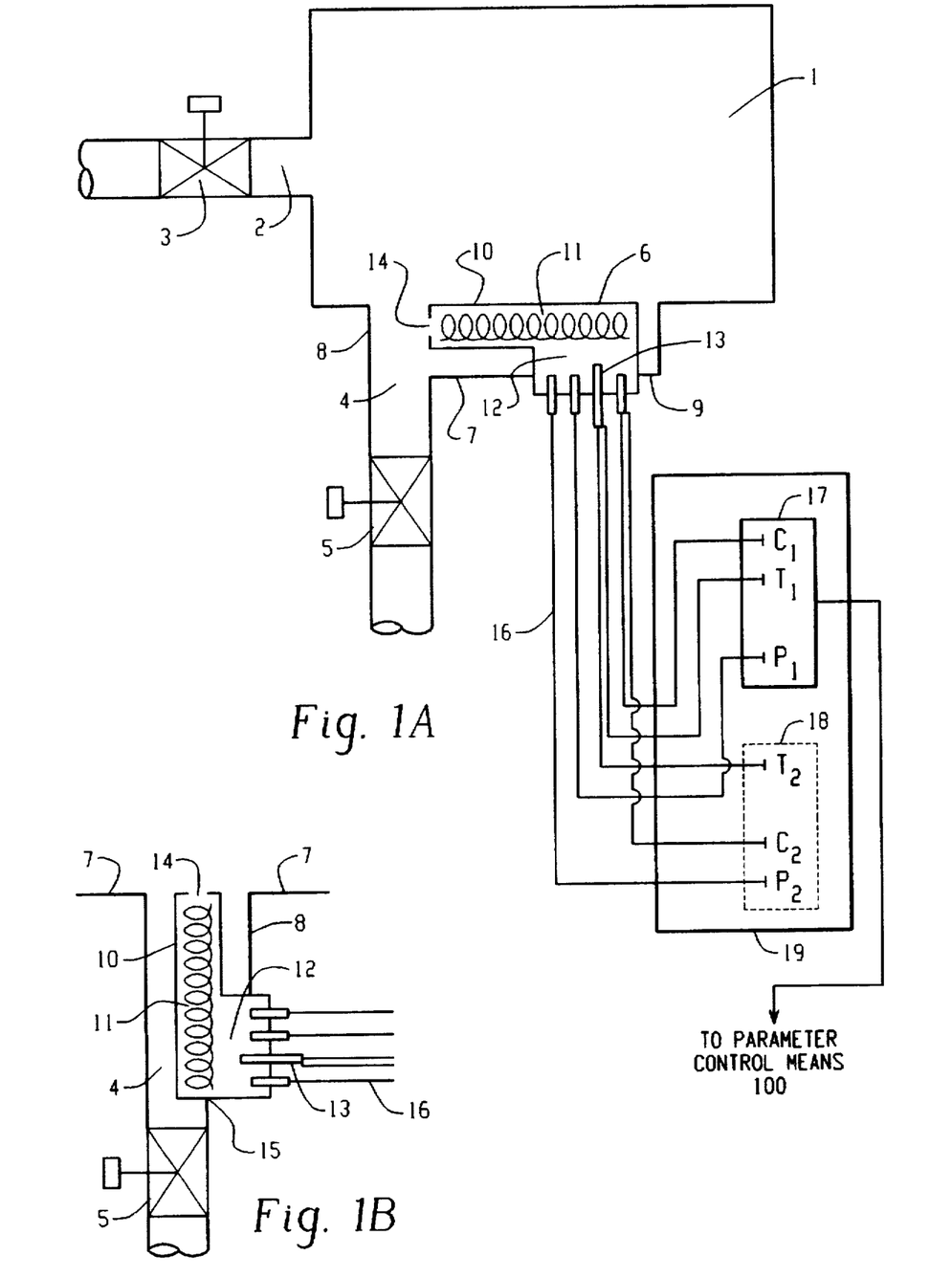
FIG. 1A is a schematic illustration of the present invention, including a load-simulating device connected to a sterilization chamber and sensor probes integrated into the sterilizer control system and a parametric release monitoring system.
FIG. 1B is a schematic illustration of a load-simulating device positioned within a sterilizer drain line.

Turning now to the drawing figures, the invention will be described in detail. As illustrated in FIG. 1A and 1B, the system includes a sterilization chamber (1) having a sterilant inlet (2) and sterilant inlet valve (3) and a chamber drain line or exhaust outlet (4) and chamber outlet valve (5). A load-simulating device (6) is located within the chamber (1) and is removably connected to a chamber wall (7) or chamber drain wall (8) as described herein below. If connected to a chamber wall (7), the load-simulating device (6) is preferably located in a recessed portion (9) of the chamber wall (7), such that the load-simulating device (6) does not interfere with loading and unloading of goods in the chamber (1). When the device (6) is employed in a steam sterilization chamber, it is more preferable to locate the device (6) close to or within the drain line (4) in order to detect more readily the presence of unwanted air that will tend to settle there, as known in the art, and allow for correction of the problem, as described herein below.

Figure 2:
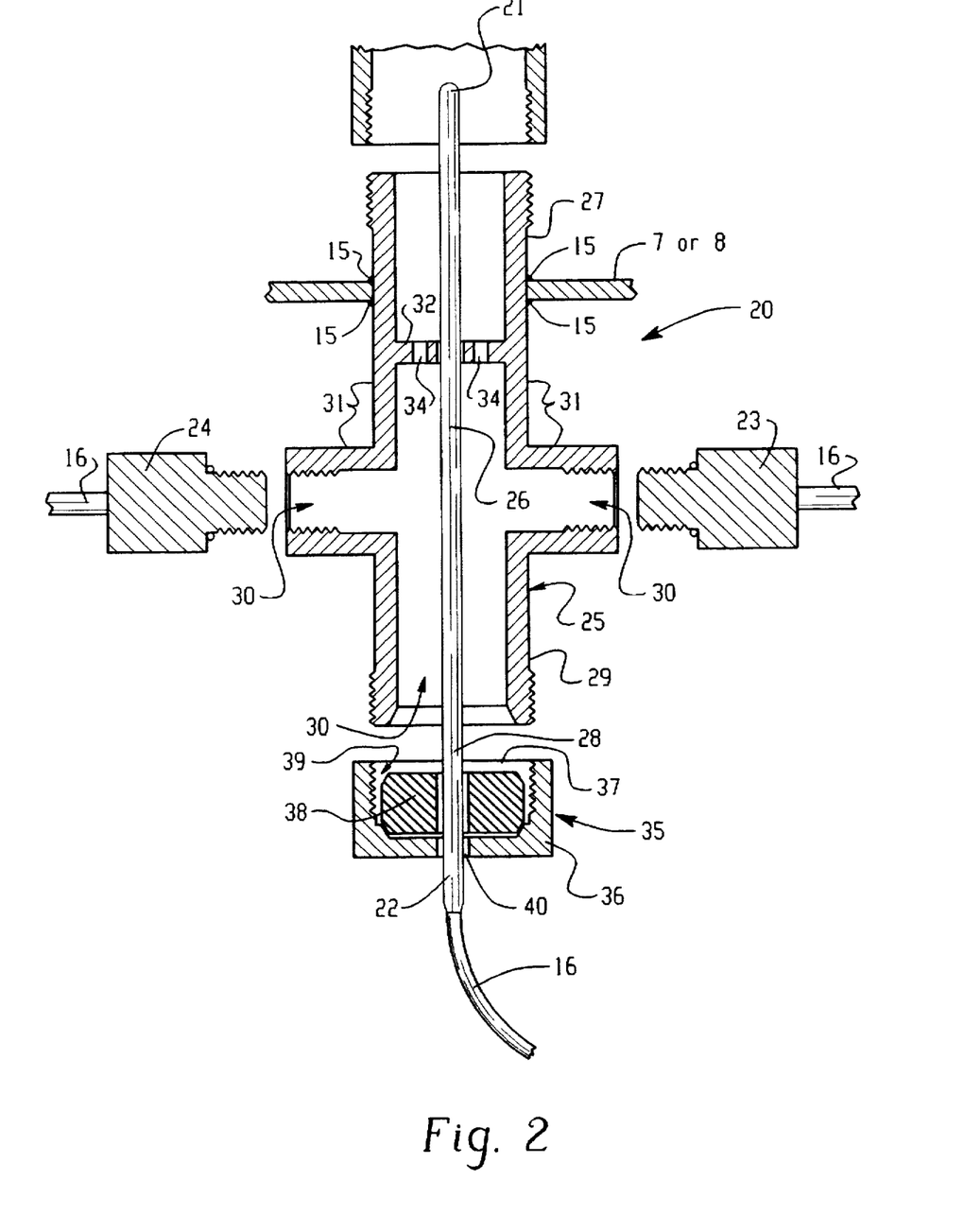
FIG. 2 illustrates an embodiment of a sensor fitting in accordance with the invention.
Figure 3A:
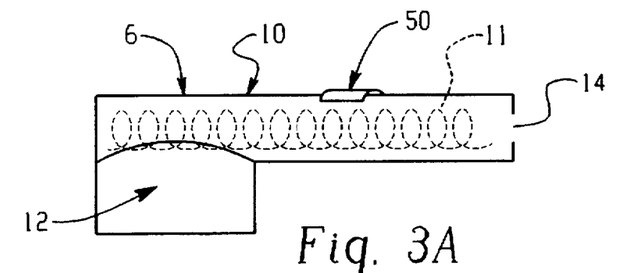
FIGS. 3A, 3B and 3C are schematic illustrations of the load-simulating device of the invention.
Figure 3B:
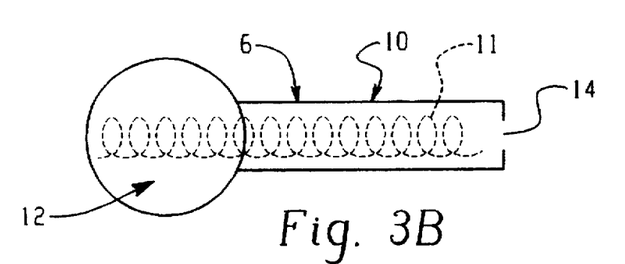

In the embodiment illustrated in FIGS. 1A and 1B, and shown schematically in FIGS. 3A and 3B, the load-simulating device (6) comprises a housing (10) for a resistance barrier (11) to penetration of a sterilant and a receiving area (12) for sterilant that successfully penetrates the resistance barrier (11). At least one sensor probe (13) is positioned in the receiving area (12) of the load-simulating device (6) for real-time sensing and monitoring of at least one sterilization parameter value during a sterilization cycle. A connection flange or a weld fillet (15) (more clearly shown in FIG. 2) connects the device (6) to the sterilization chamber wall (7) or drain line wall (8) at or near the location of the sensor probe (13). An optional use indicator (50) is preferably positioned on a surface of the load-simulating device (6) in contact with the chamber environment. The use indicator (50) serves only to indicate, preferably by a visible color change, that the load-simulating device (6) has been exposed to a sterilant. The use indicator (50) is not intended to serve as a chemical integrator.

In the embodiment illustrated in FIGS. 1A and 1B, the housing (10) of the device (6) is constructed with a small opening (14) at one end, to allow a liquid, gas or vapor sterilant to enter into the interior of the device (6). The illustrated opening in the housing is used in conjunction with the interior resistance barrier (11) that provides a tortuous path for the sterilant. However, the sterilant may alternatively enter the device by another route, preferably one that provides a tortuous path/resistance barrier, such as through a seam in the housing, or penetration by wetting through material comprising the housing wall. In this case, the additional resistance barrier (11) in the interior of the device may also be included or be optional. Therefore, the device is intended to provide one or more resistance barriers/tortuous paths, depending on the characteristics of the sterilant employed.

Regardless of the route of sterilant entry, the load-simulating device (6) itself, as defined by the housing (10), is preferably shaped to simulate a dead-ended lumen, known to be difficult to sterilize because of the known difficulty of sterilant penetration into lumens in general. Therefore, in a preferred embodiment, the device (6) itself, by virtue of simulating a dead-ended lumen, comprises a coil to resist penetration of the sterilant.

During a sterilization cycle, the liquid, gas or vapor sterilant in the sterilization chamber (1) enters the load-simulating device (6) and is constrained to follow a prescribed path. The sterilant passes through the optional resistance barrier (11) and sterilant that penetrates the barrier (11) reaches the receiving area (12) where it comes into contact with the sensor probe (13). Therefore, there is a fluid connection between the sterilization chamber (1) and the sensor probe (13).

The sensor probe (13) may be present as a single probe or a plurality of probes or sensing elements. Parameters which may be sensed by the sensor probe or probes (13) include, but are not limited to, temperature, pressure, concentration of sterilant, relative humidity and multiples and combinations of these. For example, a set of sensor probes may contain two or more pressure sensors (P1, P2) and two or more temperature sensors (T1, T2) and two or more chemical sterilant concentration sensors (C1, C2); and each parameter may be sensed by two or more separate sensing probes or by a single probe housing two or more sensing elements. As described herein below, multiple probes, preferably dual probes, for sensing a particular parameter are employed to comply with ISO and/or CEN standards requiring a separate set of sensing probes for parameter control and for parametric release of the load. Multiple probes, for example, an array of concentration-sensing elements, may be necessary in order to determine the concentration of certain chemical sterilants, such as multicomponent sterilants.

A transmitting means (16) is connected to each sensor probe or sensing element (13) for transmitting a sensed parameter value from the sensor probe (13) to a receiving means (19), such as the sterilizer control system (17) or a parametric release monitoring system (18). The transmitting means (16) may comprise any means that is capable of transmitting the sensor data to the receiving means (19) including, but not limited to, electrical connection of the sensor probe (13) to the receiving means (19) and electronic or radio frequency transmission of the sensor data to the receiving means (19).

The sterilizer control system (17) may be any system including, but not limited to, a microprocessor or a logic circuit that is programmed to receive the sensed parameter value and also to control the value of the parameter in real time during the sterilization cycle by governing a plurality of parameter control means (100) which operate valves, pumps, timers, heaters, etc. The sterilizer control system (17) is also programmed to store a predetermined reference sterilization parameter range and to compare the received sensed parameter value to the reference parameter range. If the sensed parameter value falls within the reference parameter range, acceptable sterilization conditions are indicated, and the cycle continues. If the sensed parameter value falls outside of the reference parameter range, the sterilizer control system (17) is programmed to signal the parameter control means (100) to operate until the value of the sensed parameter falls within the reference parameter range. Thus, if the sensed temperature reading in the load-simulating device (6) is below an acceptable limit, the sterilizer control system (17) signals the parameter control means (100) to operate a chamber heating means (not shown) until the temperature reading of the temperature-sensing probe (13) in the load-simulating device falls within the range that is acceptable for sterilization. If a sensed sterilant concentration in the load-simulating device (6) is below the acceptable limit, the sterilizer control system (17) signals the parameter control means (100) to control the operation of a sterilant injector (not shown) to increase the concentration of sterilant injected into the chamber (1), until the concentration of sterilant sensed by the concentration-sensing probe (13) is at an acceptable value, or within a range of acceptable values. In each of these examples, the sterilizer control system (17) also signals a timer (not shown) to be reset to compensate for the time during which the sterilization cycle experienced unacceptable conditions. In many sterilization cycles, critical parameters are interdependent. For example, in a vapor hydrogen peroxide sterilization system, the concentration of the vapor that is allowable (i.e. does not exceed the dew point concentration) in the load at any given time is dependent on the temperature, pressure, and/or relative humidity in the load at that time. Therefore, in systems such as these, the sterilizer control system is programmed to monitor more than one parameter and analyze the data to determine whether or not the environmental conditions are within the acceptable range of values.

In each embodiment of the invention, a redundant set or sets of temperature, pressure or other sensors (13), such as relative humidity or chemical sterilant concentration sensors may be incorporated. For example, in a preferred embodiment as illustrated in FIG. 1A, one set of sensor probes (T2, P2, C2) is used only as a parametric release monitoring system (18), for monitoring sterilization parameters to determine if acceptable sterilization conditions in the load-simulating device (6) have been achieved and the load may be released as sterilized. Another set of sensors probes (T1, P1, C1) in the load-simulating device (6) transmits readings of temperature, pressure or other parameter levels to the sterilizer control system (17) for controlling the process parameters by the parameter control means (100). In this embodiment, the release monitoring sensors (T2, P2, C2) are preferably connected to a user interface (display and/or printout) circuit (not shown) which is separate from the circuit (not shown) that connects the sterilizer control system (17) and the sensors (T1, P1, C1) that provide data for process control. This feature addresses the concern outlined in current CEN and ISO standards for the need to keep the parametric release system independent of the system that controls the sterilizer cycle. The independent release monitoring sensors act as a back-up and redundant system to the sensors integrated into the sterilizer control system. Thus, erroneous release of a load that is not sterilized because sensors used for control purposes falsely indicate (e.g. due to being out of calibration or subject to a component or electrical failure) that sterilization conditions are being achieved, is virtually prevented.

FIG. 2 illustrates an embodiment of one possible sensor fitting (20) for use in the present invention, for containing at least one (22), and preferably a plurality of sensor probes (22, 23, 24), and for attaching the sensor probe or probes to the load-simulating device (6), and to the chamber wall (7) or drain wall (8). It is envisioned that any sensor fitting which is capable of accommodating the sensor probes and load-simulating device and accomplishing the objectives of the invention, may be alternatively used in the practice of the invention. In the illustrated embodiment, at least one each of a temperature sensor probe (22), a pressure sensor probe (23) and a chemical sterilant concentration sensor probe (24) are used in the practice of the invention. However, these probes are meant to be representative only, and are interchangeable with probes measuring other parameters, such as relative humidity. They may also represent a plurality of one or more types of probes, such as a plurality of concentration-sensing probes for different components of a multicomponent chemical sterilant, or a plurality of temperature or pressure sensing probes.

As illustrated in FIG. 2, this embodiment of the sensor fitting (20) comprises a housing (25) having an outer wall and an interior wall which defines a hollow interior having a first end (27) and a second end (29) and side walls (31). The first end (27) of the sensor fitting (20) is shaped to protrude into the interior of the chamber (1) through a complementary opening in the chamber wall (7) or chamber drain wall (8). The outer wall of the housing (25) is secured to the chamber wall (7) or drain wall (8) by means of a connection flange or a weld fillet (15) that provides a seal between the sensor fitting (20) and the chamber wall (7) or drain wall (8). The second end (29) of the sensor fitting (20) extends exteriorly from the chamber wall (7) or drain wall (8). The first end (27) and second end (29) and the side walls (31) of the sensor fitting (20) comprise openings (30) for receiving a sensor probe or plurality of sensor probes (see below). As illustrated in this embodiment, a temperature sensor probe (22) extends through the hollow interior of the length of the sensor fitting (20) and comprises a tip portion (21) which protrudes beyond the open first end (27) of the sensor fitting (20), a middle portion (26) contained within the hollow interior of the sensor fitting (20), and a base portion (28) which extends beyond the open second end of the sensor fitting (20). The position of the temperature probe (22) within the hollow sensor fitting (20) may be optionally stabilized by means of a support flange (32), connected to an interior wall of the housing (25), containing a plurality of openings (34) sufficient to ensure that a fluid environment is maintained throughout the hollow interior of the sensor fitting (20).

As described herein above, the housing (25) of the sensor fitting (20) comprises an opening or a plurality of other openings (30) for receiving other sensor probes. The probes illustrated in FIG. 2 include, but are not limited to, a pressure sensing probe (23) and/or a chemical sterilant concentration sensing probe (24). Each of the sensor probes (23, 24) is in fluid connection with the hollow interior of the sensor fitting (20) and is engaged, preferably threadably engaged, to the housing (25) to form a seal between the sensor probe (23, 24) and the sensor fitting (20). Each of the sensor probes (22, 23, 24) terminates in a separate transmission means (16), extending from each probe and external to the sensor fitting (20) for transmitting sensed data to the receiving means (19).

The base portion (28) of the temperature probe (22), including the transmitting means (16), further extends through a compression fitting (35) comprising a housing (36) defining an anterior opening (37) containing a flexible ring member (38), preferably a ferrule, that encircles the base portion (28) of the probe (22) and a space (39) surrounding the ring member (38), and a posterior opening (40) for affording the passage of the base portion (28) of the temperature probe (22) therethrough, the transmission means (16) extending exteriorly from a posterior opening (40). The compression fitting (35) is removably engagable to the second end (29) of the sensor fitting (20). A pressure-tight seal between the compression fitting (35) and the sensor fitting (20) is achieved when the second end (29) of the sensor fitting (20) threadably engages the anterior opening (37) of the compression fitting (35), occupies the space (39) between the housing (36) and the ring member (38) and, thereby, sealably compresses the ring member (38) around the temperature probe (22).

As described herein above, the first end (27) of the sensor fitting (20) is shaped to protrude into the interior of the chamber (1) through a complementary opening in the chamber wall (7) or chamber drain wall (8). The first end (27) of the sensor fitting (20) is also removably and sealably connectable, preferably threadably connectable, to the load-simulating device (6) within the chamber (1). As described herein above, the tip portion (21) of the temperature probe (22) extends beyond the first end (27) of the sensor fitting (20). In a preferred embodiment, when the sensor fitting (20) is connected to the load-simulating device (6), the tip portion (21) of the temperature probe (22) extends into the receiving area (12) of the load-simulating device (6) but does not contact or extend into the resistance barrier (11).

When a sensor fitting (20) such as that described in FIG. 2 is employed, there are a number of possible embodiments for the inter-connection of the sensor probes (13), the load-simulating device (6), and the transmitting means (16). For example, in one embodiment schematically illustrated in FIG. 1A, the sensor probes (13) including the transmission means (16) connecting the probes (13) to the sterilizer control system (17) are preconnected and premounted via the sensor fitting (20) of FIG. 2 to the chamber wall (7) or drain line (8). Thus, the load-simulating device (6) is removably connected to the premounted sensor fitting (20) inside the chamber wall (7) or drain wall (8) at the location of the probes (13) in the manner illustrated in the embodiment of FIG. 2. In this embodiment, the load-simulating device may be, and preferably is, disposable. Alternatively the device may be reusable if, for example, it is recharged or dried out (in the case of a sterilization cycle involving moisture). The sensor probes may be permanently or temporarily mounted to the chamber, as desired.

Figure 3C:
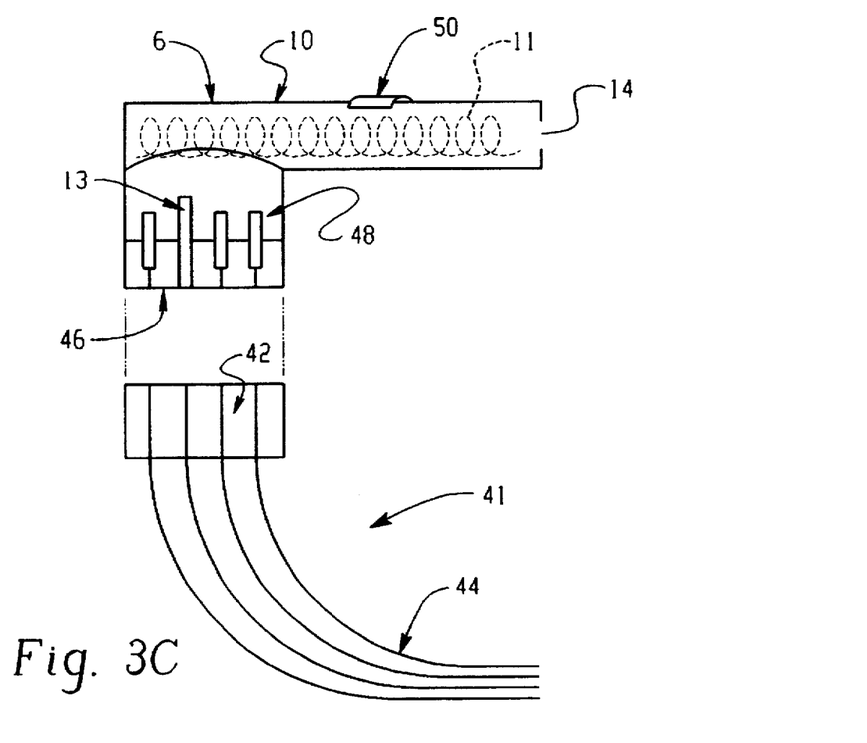

In another embodiment, schematically illustrated in FIG. 3C, sensor probes (48) are removably connectable to the load-simulating device as illustrated in FIG. 2 and described herein above. However, in this embodiment, a sensor connector (41), which may extend into the interior of the chamber, has a electrical connector portion (42) connected to the chamber wall (7) or drain line (8), and a signal transmission means portion (44) connectable to a signal receiver (not shown). The sensor probes (48) terminate in one or more complimentary electrical interface(s). Thus, in this embodiment, the sensor probes (48) may be preconnected to a load-simulating device and then interfaced to the sterilizer control via an electrical connection inside the chamber. In this embodiment, the sensor probes may also be reusable and/or disposable.

Figure 4A:
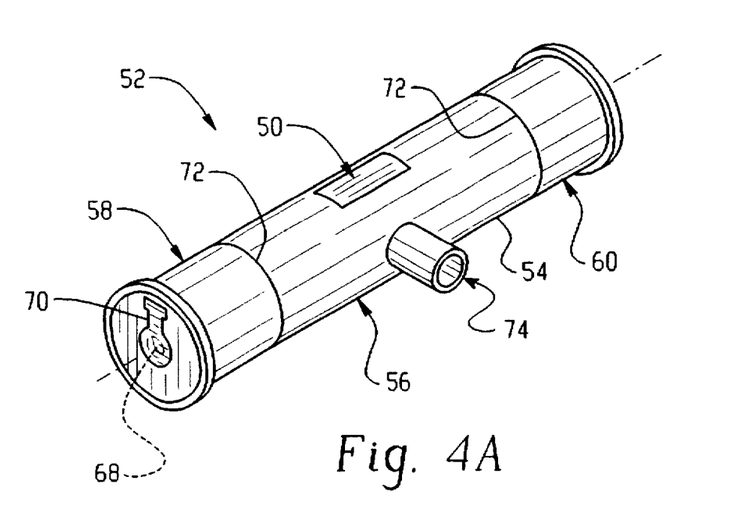
FIGS. 4A and 4B illustrate an embodiment of a load-simulating device of the invention in a closed configuration and an exploded view, respectively.
Figure 4B:
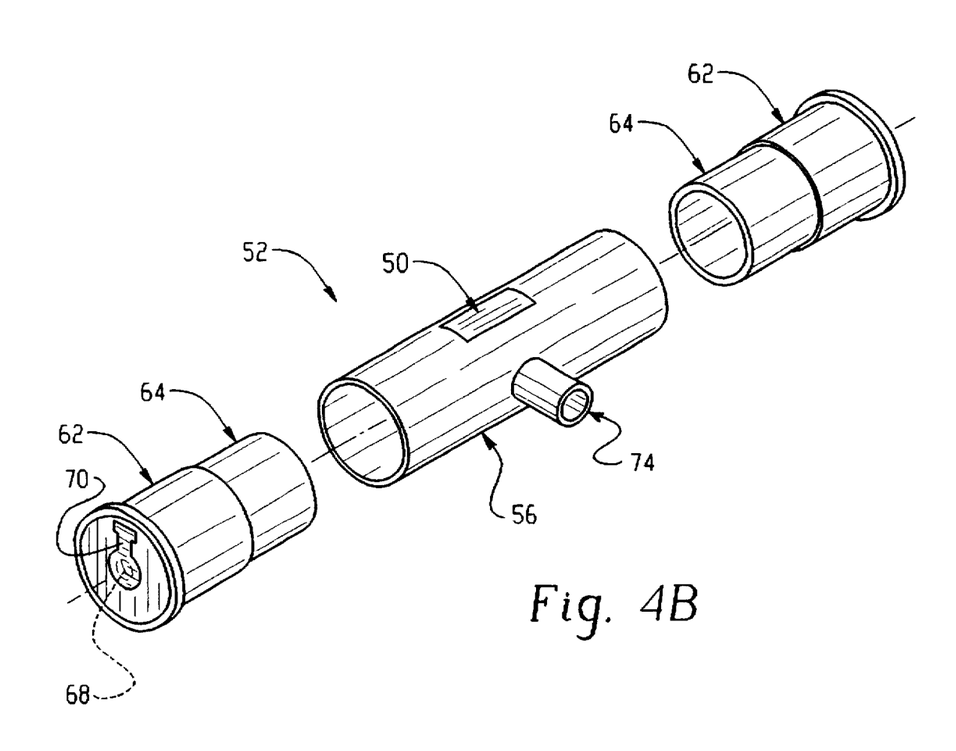
Figure 5A:
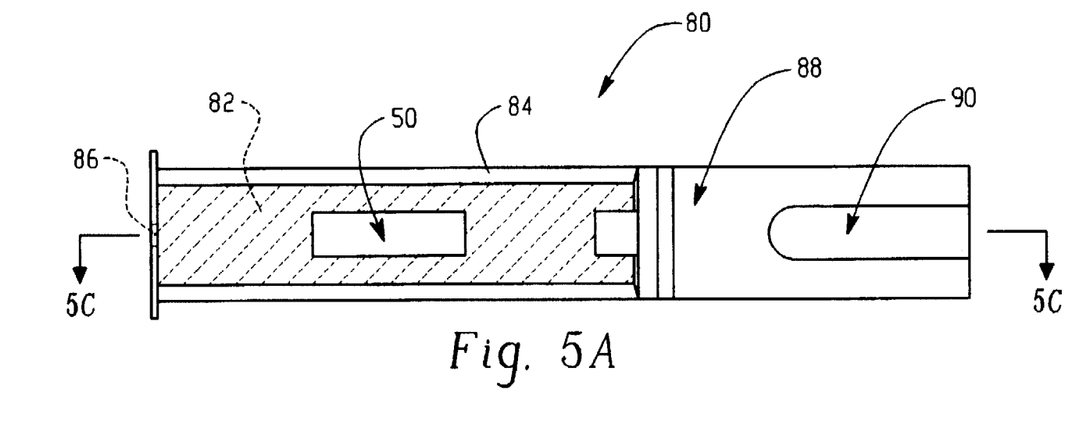
FIGS. 5A, 5B and 5C schematically illustrate another embodiment of a load-simulating device of the invention.
Figure 5B:
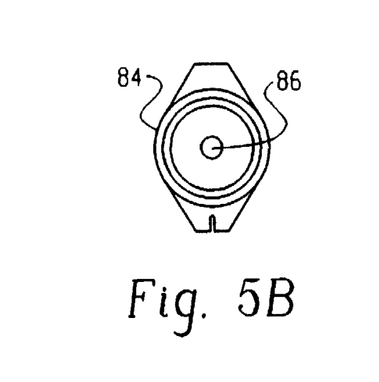
Figure 5C:
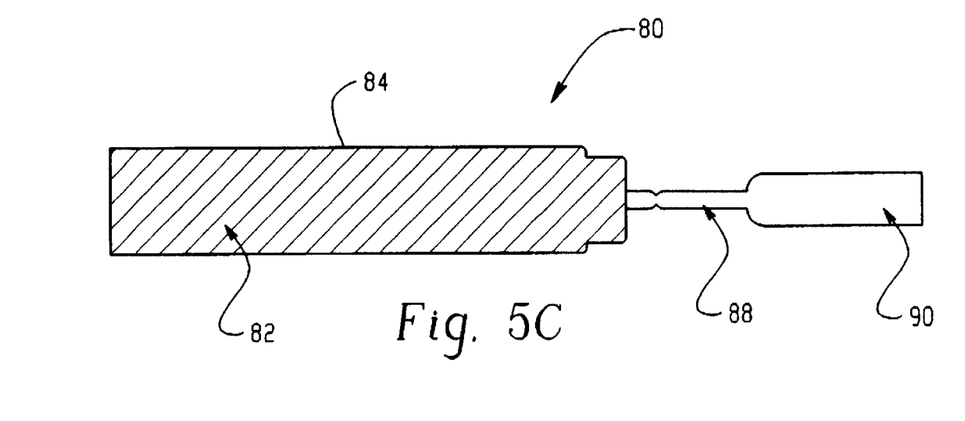

FIGS. 4 and 5 illustrate embodiments of a load-simulating device which may be employed in the present invention. The precise nature of the load-simulating device to be used for a given sterilization cycle depends on the nature of the sterilant and the sterilization parameters to be monitored. For example, a load-simulating device for a steam sterilization cycle, a hydrogen peroxide vapor sterilization cycle and an ethylene oxide sterilization cycle, etc. may be different from each other, because of different critical sterilization parameters and sterilant properties. Thus, for steam, the resistance barrier in the load-simulating device preferably comprises a barrier material, such as a cellulosic, that absorbs heat, and the sensors within the device preferably monitor and provide for control of both temperature and pressure within the device. For an ethylene oxide sterilant, a tortuous path for penetration of the sterilant into and through the device preferably comprises a physical barrier to the flow of the gas. The materials selected for the barrier are determined by the solubility and diffusion rate of the ethylene oxide in the material and the thickness of the barrier. For example, ethylene oxide has a higher diffusion rate through silicon than through polyethylene, so polyethylene is preferable to silicon as a barrier material. The sensor probes employed for an ethylene oxide cycle preferably monitor and provide for control of temperature, pressure, relative humidity and concentration of the sterilant within the load-simulating device.

A preferable load-simulating device for hydrogen peroxide liquid or vapor sterilization includes a dead-ended device and a resistance barrier comprising a physical restriction of the flow of the sterilant (e.g. through a restricted orifice or orifices) and/or requiring changes in direction of flow (e.g. around baffles). The preferred materials of construction of the resistance barrier comprise those which inhibit gas penetration and do not substantially absorb the sterilant. Thus, for hydrogen peroxide sterilization, polyethylene, polypropylene, teflon, silicon, and polycarbonate are preferred materials. The sensor probes employed for a vapor hydrogen peroxide cycle preferably monitor and provide for control of temperature, pressure, relative humidity and concentration of the sterilant within the load-simulating device.

The preferred load-simulating devices generally include a housing defining one or more resistance barriers to the passage of a sterilant and a receiving area where sterilant which has penetrated the resistance barrier(s) comes into contact with one or more sensor probes. As described herein above, one of the resistance barriers may be a dead-ended lumen defined by the housing.

The load-simulating device shown in FIG. 4A in a closed configuration and in FIG. 4B in an exploded view is illustrative of a housing comprising a tortuous path for entry of a sterilant into the interior of the device. A typical exterior housing for use in a steam or ethylene oxide sterilization cycle is disclosed in commonly owned U.S. Pat. Nos. 4,839,291 and 4,914,034, the disclosures of which pertaining to tortuous paths through the housing of the device are hereby incorporated by reference. In brief, the housing (54) of a canister (52) comprises a central tubular portion (56), a first tubular end portion (58) and a second tubular end portion (60). The central tubular portion (56) has two open ends. Each of the tubular end portions (58, 60) includes an outer member (62) having a closed end, and an inner member (64) having an open end. The outer member (62) of tubular end portion (58) further has a hole or opening (68) in its closed end that is covered with an adhesive backed tab (70). The tab (70) permits the optional opening or closure of hole (68). The inner members (64) of each of the end portions (58, 60) telescope into the central tubular portion (56) of the housing (54) allowing each of the outer members (62) to abut the central tubular portion (56) and form a seam or gap (72) between the central tubular portion and the outer members (62) of the tubular end portions (58,60). The seam or gap (72) forms a tortuous path for entry of the sterilant into the interior of the canister (52). Further, the seam or gap (72) may optionally be covered by a sterilant-permeable layer (not shown), such as medical grade paper, to form a further tortuous path for entry of the sterilant into the interior. Another tortuous path for entry of the sterilant is defined by the close tolerance between the telescoping surfaces of the central tubular portion (56) and inner members (64) of the end portions (58, 60) of the housing (54). As practiced in the present invention and described herein previously, the device may optionally contain a further resistance barrier (not shown) to sterilant passage, such as a packed material or a baffle or series of baffles, within the interior of the device. Preferably, such an internal resistance barrier is employed when the sterilant enters the canister through opening (68) when tab (70) is removed.

The central tubular portion (56) of the canister (52) illustrated in FIG. 4 includes a connection fitting (74) that is removably connectable to a sensor fitting, as illustrated in FIG. 2. The device optionally has a use indicator (50) positioned on an exterior surface.

FIGS. 5A, 5B and 5C illustrate another embodiment of a load-simulating device which incorporates a tortuous path in the interior of the device. A typical device may include a tortuous path as described for a steam sterilization cycle disclosed in commonly owned U.S. Pat. No. 4,594,223, the disclosure of which pertaining to tortuous paths is hereby incorporated by reference. However, the tortuous path may be different from the disclosed device (e.g. baffles, etc.) depending on the sterilant employed, as described herein above. Briefly, the device (80) comprises a resistance barrier (82) within a canister housing (84) and a use indicator (50) on the exterior of the canister. One end of the housing (84) is in fluid communication with the chamber environment and has an opening (86) for the passage of a sterilant into and through the length of the device. The receiving area (88) for sterilant fluidly penetrating the resistance barrier (82) has a connection fitting (90) at the opposite end for removable attachment to a sensor fitting as shown in FIG. 2. As shown in cross-section in FIG. 5C, the receiving area (88) is constricted to prevent resistance barrier material from entering the receiving area. As more fully described in U.S. Pat. No. 4,594,223, if steam sterilization is employed the constriction also serves as a collection area for any unwanted air mixed with the steam, the air being in fluid contact with the sensors, to allow control of the cycle for correction of the problem or aborting of the cycle.

The materials from which the housing of the load-simulating device and/or any internal resistance barrier are manufactured may be different from each other and are selected to be compatible with the sterilant employed. The housing material may be slightly absorptive of the sterilant, but may not be so absorptive as to affect the concentration level of sterilant in the chamber in the area surrounding the device or to result in high levels of residual sterilant which may be difficult to remove at the completion of the sterilization cycle. Suitable, and preferred, housing and/or resistance barrier materials may include, but are not limited to, cellulosic materials for steam and/or ethylene oxide sterilants; teflon, silicon, polypropylene and polycarbonate materials for ethylene oxide and hydrogen peroxide sterilants; and combinations thereof.

Figure 6:
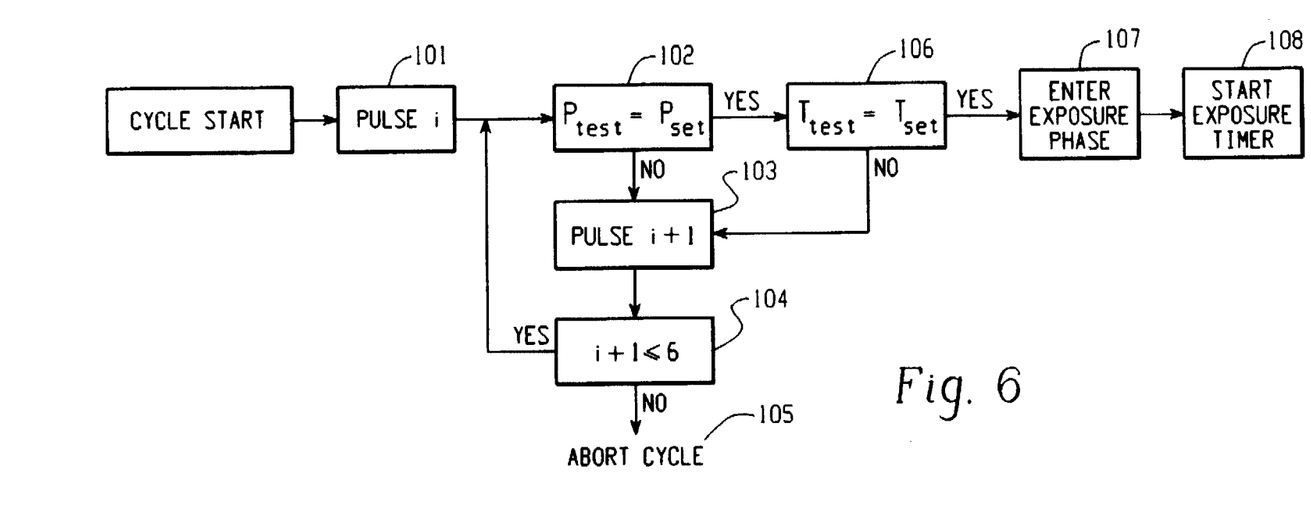
FIG. 6 illustrates an example of the pre-exposure phase of a steam sterilization cycle which may be employed in the invention.
Figure 7:
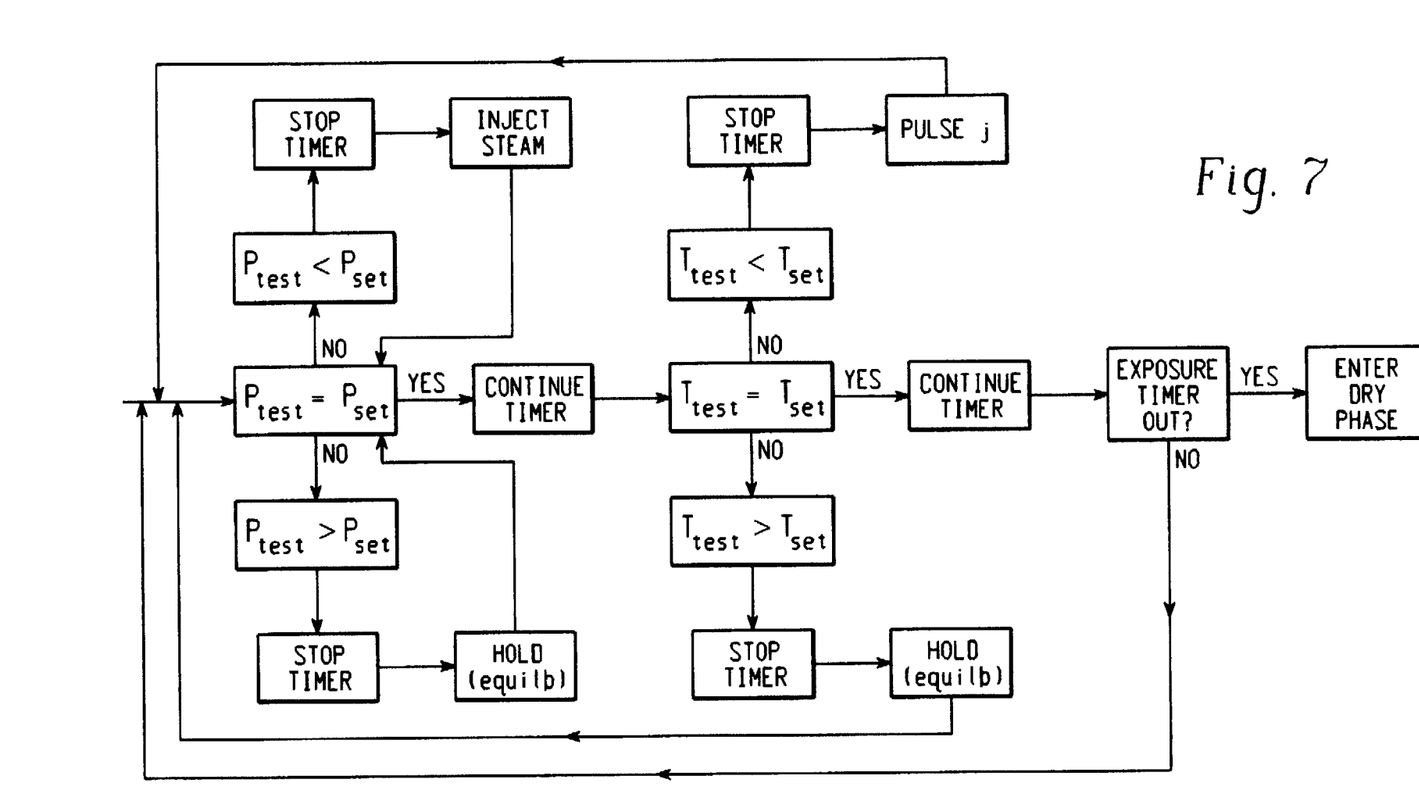
FIG. 7 illustrates an example of the exposure phase of a steam sterilization cycle which may be employed in the invention.
Figure 8:
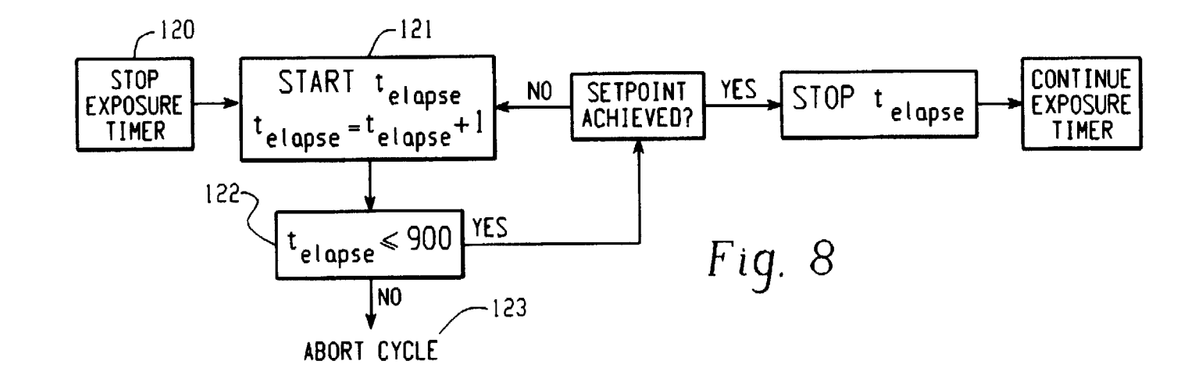
FIG. 8 illustrates an example of a timing cycle which may be employed in the invention.

FIGS. 6, 7, and 8, illustrate the method of the invention in a typical steam sterilization cycle employing the real-time monitoring and control of cycle parameters within the load-simulating device and parametric release of the load for use when the parameters are met. Although a steam sterilization cycle is illustrated, the method of the invention can be modified by one skilled in the art to accommodate any sterilant, such as ethylene oxide, hydrogen peroxide, formaldehyde, ozone, peroxy compounds, and the like. For a steam sterilization cycle, the parameters of temperature, pressure and time are preferably monitored. For an ethylene oxide cycle, the parameters of temperature, pressure, relative humidity, time, and the concentration of ethylene oxide are preferably monitored. For a chemical sterilant, such as liquid or vaporized formaldehyde or liquid or vaporized hydrogen peroxide, the parameters of temperature, pressure, relative humidity, time, and the concentration of the sterilant are preferably monitored.

As illustrated in FIG. 6, the method of the invention begins with a pre-exposure phase pulse (number "i") (101) which, for a pre-vacuum type sterilizer is typically a vacuum pull and steam charge, and for a gravity type sterilizer is typically a steam flush with an open drain line. Following "Pulse i", the pressure in the load-simulating device (test device) is sensed by the pressure probe. If, for example due to air in the device, the sensed pressure ($P_{test} \pm Z$ psia) does not fall within an acceptable predetermined setpoint pressure ($P_{set} \pm Z$ psia) range, the sterilizer control system signals the parameter control means (100) to produce another pulse (i+1) (103). Extra pulses continue only until the pressure sensor indicates that $P_{test} = P_{set}$ (102). The number of extra pulses is limited (to six or less, in the illustration) (104) or the cycle is aborted (105) in order to prevent an infinite cycle which could occur, for example, in the event of a chamber air leak. When $P_{test} = P_{set}$ (102), a pass situation is indicated, and the temperature is sensed by the temperature probe. If the sensed temperature ($T_{test} \pm Y°C$) does not fall within an acceptable predetermined setpoint temperature ($T_{set} \pm Y°C$) range, for example due to the presence of air in the device, the sterilizer control system signals the parameter control means (100) to produce another pulse. When $T_{test} = T_{set}$ (106), a pass situation is indicated and the cycle enters the exposure phase (107) illustrated in FIG. 7 and starts the exposure timer (108). The same principles of pass/fail apply to the sensed pressure and temperature in the load-simulating device during this exposure phase. Whenever the sensed pressures or temperatures are not acceptable, the exposure timer is stopped (120) for the time required to bring the parameters into the acceptable range, as illustrated in FIG. 8. If the elapsed time ($T_{elapse}$) (121) exceeds a certain set point (900 seconds, in the example) (122), the cycle is aborted (123), in order to avoid an infinite cycle.

Throughout the cycle, the monitoring sensors in the load-simulating device transmit data to a receiving means comprising a parametric release sensing system. When the data indicate that the critical parameters of the cycle have been achieved in the load-simulating device, the parametric release system presumes the load has been sterilized. The parametric release monitoring system thus allows release of the load for use when the monitored sterilization parameter levels indicate sterilization cycle efficacy within the load-simulating device.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

We claim:

1. A method of monitoring and controlling a sterilization parameter value in a simulated load during a hydrogen peroxide vapor sterilization cycle, comprising the steps of:
  (a) providing a challenge load-simulating device in a sterilizer, said device comprising a resistance (barrier to penetration of hydrogen peroxide vapor and a receiving area for hydrogen peroxide vapor that penetrates the resistance barrier;
  (b) sealably fitting a first sensor probe within said device, such that said sensor probe is positioned in said receiving area for real-time sensing therein of a sterilization parameter value during a sterilization cycle, said sensor probe comprising a transmitting means for transmitting the sensed parameter value from the sensor probe to a sterilizer control system;
  (c) exposing the load-simulating device to hydrogen peroxide vapor during a sterilization cycle;
  (d) sensing the sterilization parameter value within the receiving area of the device during the sterilization cycle;
  (e) transmitting the sensed sterilization parameter value in the load-simulating device from the sensor probe to the sterilizer control system; and
  (f) controlling the value of the sterilization parameter in real time during the sterilization cycle in response to a signal from the sterilizer control system;

wherein the sterilizer control system is programmed to store a predetermined reference sterilization parameter range; the sterilizer control system being further programmed to receive the sensed parameter value and compare the sensed parameter value to the stored reference parameter range; the sterilizer control system being further programmed to indicate acceptable sterilization conditions when the sensed parameter value falls within the reference parameter range; the sterilizer control system being further programmed to signal the parameter control means to change the value of the sterilization parameter when the sensed parameter value falls outside the reference parameter range.

2. The method of claim 1, further comprising the steps of sealably fitting a second sensor probe within said device, such that said second sensor probe is positioned in fluid communication with said receiving area for real-time sensing therein of a sterilization parameter value during the sterilization cycle, said sensor probe comprising a second transmitting means connected to the second sensor probe; sensing the sterilization parameter value during the sterilization cycle; transmitting the sensed sterilization parameter value in the load-simulating device from the second sensor probe to a receiving means comprising a parametric release monitoring system; and releasing the load for use when the monitored sterilization parameter levels indicate sterilization cycle efficacy.

3. A method of monitoring and controlling a sterilization parameter value in a simulated load during a hydrogen peroxide vapor sterilization cycle, comprising the steps of:

(a) providing a challenge load-simulating device in a sterilizer, said device comprising a resistance barrier to penetration of hydrogen peroxide vapor and a receiving area for hydrogen peroxide vapor that penetrates the resistance barrier;

(b) sealably fitting a first sensor probe within said device, such that said sensor probe is positioned in said receiving area for real-time sensing therein of a sterilization parameter value during a sterilization cycle, the sterilization parameter being selected from the group consisting essentially of temperature, pressure, relative humidity, sterilant concentration, time and multiples and combinations thereof, said sensor probe comprising a transmitting means for transmitting the sensed parameter value from the sensor probe to a sterilizer control system;

(c) exposing the load-simulating device to hydrogen peroxide vapor during a sterilization cycle;

(d) sensing the sterilization parameter value within the receiving area of the device during the sterilization cycle;

(e) transmitting the sensed sterilization parameter value in the load-simulating device from the sensor probe to the sterilizer control system; and (f) controlling the value of at least one of temperature, pressure, and sterilant concentration in real time during the sterilization cycle in response to a signal from the sterilizer control system:

the sterilizer control system being programmed to store a predetermined reference sterilization parameter range; the sterilizer control system being further programmed to receive the sensed parameter value and compare the sensed parameter value to the stored reference parameter range; the sterilizer control system being further programmed to indicate acceptable sterilization conditions when the sensed parameter value falls within the reference parameter range; the sterilizer control system being further programmed to signal the parameter control means to change the value of the sterilization parameter when the sensed parameter value falls outside the reference parameter range.

4. A method of monitoring and controlling a sterilization parameter value in a simulated load during a sterilization cycle, comprising the steps of:

(a) providing a challenge load-simulating device in a sterilizer, said device comprising a resistance barrier to penetration of a sterilant and a receiving area for sterilant that penetrates the resistance barrier;

(b) sealably fitting a first sensor probe within said device, such that said sensor probe is positioned in said receiving area for real-time sensing therein of a sterilization parameter value during a sterilization cycle, said sensor probe comprising a transmitting means for transmitting the sensed parameter value from the sensor probe to a sterilizer control system;

(c) during a sterilization cycle, exposing the load-simulating device to a sterilant selected from the group consisting essentially of steam, ethylene oxide gas, liquid hydrogen peroxide, vaporized hydrogen peroxide, liquid formaldehyde, vaporized formaldehyde, liquid peroxy compounds, vaporized peroxy compounds, ozone, ionized gases, plasmas, and combinations thereof;

(d) sensing the sterilization parameter value within the receiving area of the device during the sterilization cycle;

(e) transmitting the sensed sterilization parameter value in the load-simulating device from the sensor probe to the sterilizer control system; and (f) controlling the value of the sterilization parameter in real time during the sterilization cycle in response to a signal from the sterilizer control system;

the sterilizer control system being programmed to store a predetermined reference sterilization parameter range; the sterilizer control system being further programmed to receive the sensed parameter value and compare the sensed parameter value to the stored reference parameter range; the sterilizer control system being further programmed to indicate acceptable sterilization conditions when the sensed parameter value falls within the reference parameter range; the sterilizer control system being further programmed to signal the parameter control means to change the value of the sterilization parameter when the sensed parameter value falls outside the reference parameter range.

5. A method of monitoring and controlling a sterilization process in a sterilization chamber, the method comprising:

placing in the chamber a challenge load-simulating device that has a baffle that is resistant to penetration by a sterilant vapor and a receiving area for receiving sterilant vapor that penetrates the baffle;

conducting a sterilization cycle in the chamber;

during the sterilization cycle, sensing the concentration of the sterilant vapor in the receiving area and generating an electronic sterilization parameter value in response thereto; and, controlling at least one of vapor concentration, chamber temperature, and cycle duration in real-time in response to the sensed parameter value.

6. A method for monitoring or controlling a sterilization process utilizing hydrogen peroxide vapor in a chamber having an interior and a sensor disposed within said chamber and separate from a load to be sterilized, said sensor providing a real-time control signal representative of at least one sterilization parameter, said method comprising:

applying a resistance barrier between said sensor and said chamber interior, wherein said resistance barrier comprises a series of spaced baffles that define a tortuous path that impedes penetration of hydrogen peroxide vapor from said chamber interior to said sensor.

7. The method of claim 6 further comprising:

selecting said resistance barrier to simulate load conditions encountered by said sterilant, wherein said resistance barrier is shaped to simulate a dead-ended lumen.

8. The method of claim 6 further comprising:

selecting said resistance barrier to simulate load conditions encountered by said sterilant, wherein said resistance barrier is in the form of a coil.

9. A method of monitoring a sterilization parameter in a sterilization system including a sensor which (i) measures said sterilization parameter and (ii) provides a real-time control signal representative of said sterilization parameter, said method comprising:

selecting a resistance barrier to simulate the barrier encountered by a sterilant when penetrating a load, said resistance barrier including a series of baffles that define a tortuous path;

disposing said resistance barrier between said sensor and said sterilant; and monitoring said control signal provided by said sensor.

10. The method of claim 9 further including controlling at least one of exposure time of articles undergoing sterilization in the system, temperature in the system, and sterilant concentration in response to the control signal.

11. The method of claim 10 wherein the resistance barrier is shaped to simulate a dead-ended lumen.

12. The method of claim 10 wherein the resistance barrier is in the form of a coil.

13. The method of claim 9 wherein the resistance barrier is shaped to simulate a dead-ended lumen.

14. The method of claim 9 wherein the resistance barrier is in the form of a coil.

* * * * *